United States Patent
Wang et al.

(10) Patent No.: US 8,877,163 B2
(45) Date of Patent: Nov. 4, 2014

(54) CYCLOALKYL TRIAMINE PENTACARBOXYLATE AS LIGANDS FOR PARAMAGNETIC METAL COMPLEXES

(75) Inventors: Yun-Ming Wang, Fengshan (TW); Chih-Wei Chiu, Taipei (TW); Gin-Chung Liu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 2390 days.

(21) Appl. No.: 11/524,771

(22) Filed: Sep. 21, 2006

(65) Prior Publication Data

US 2007/0207087 A1   Sep. 6, 2007

(30) Foreign Application Priority Data

Mar. 1, 2006   (TW) ................ 95106893 A

(51) Int. Cl.
*A61B 5/055*   (2006.01)
*C07F 5/00*   (2006.01)
*C07F 1/00*   (2006.01)
*C07F 11/00*   (2006.01)
*C07F 15/00*   (2006.01)
*A61K 49/10*   (2006.01)

(52) U.S. Cl.
CPC .................... *A61K 49/103* (2013.01)
USPC .......... 424/9.364; 534/16; 556/116; 556/148; 556/63

(58) Field of Classification Search
None
See application file for complete search history.

(56) References Cited

U.S. PATENT DOCUMENTS

| 6,162,947 | A | 12/2000 | Ausonio et al. |
| 6,303,761 | B1 | 10/2001 | Wang et al. |
| 2003/0194371 | A1* | 10/2003 | Lehmann et al. ............ 424/1.11 |
| 2004/0258620 | A1 | 12/2004 | Lehmann et al. |

FOREIGN PATENT DOCUMENTS

TW   490454   6/2002

OTHER PUBLICATIONS

Dorwald F.A., "Side Reactions in Organic Synthesis", 2005, Wiley: VCH, Weinheim p. IX of preface.*
Heylin, M., et al., "Chemistry grads post gains in 2006", 2004, Chemical and Engineering News, pp. 43-52.*
Merriam-Webster Online Dictionary entry for "derivative", (http://www.merriam-webster.com/dictionary/derivative), last accessed May 12, 2010.*
Aime, S., et al., "Contrast agents for magnetic reosnance . . . ", 1999, JBIC, 4, pp. 766-774.*
Wang, Y-M, et al. 1998. "Synthesis and complexation of $G^{3+}$, $Ca^{2+}$, $Cu2^{2+}$, and $Zn^{2+}$ by 3,6,10-tri(carboxymethyl)-3,6,10-triazadodecanedioic acid", *J. Chem. Soc.*, Dalton trans., pp. 4113-4118.
Cacheris, W. P., et al. 1990. "The Relationship Between Thermodynamics and the Toxicity of Gadolinium Complexes", *Magnetic Resonance Imaging*, vol. 8, pp. 467-481.
Schauer, C. K. et al. 1989. "Highly Polydentate Ligands. Part 4. Crystal Structures of Neodymium(*m*) and Erbium(*m*) complexes of 3, 12-Bis(carboxymethyl)-6,9-dioxa-3, 12-diazatetradecanedioate(4-)" *J. Chem. Soc.*, Dalton trans., pp. 185-191.
Toth, E. et al. 2001. "Similarities and differences between the isoelectronic $Gd^{III}$ and $Eu^{II}$ complexes with regard to MRI contrast agent applications" *Coordination Chemistry Reviews*, pp. 363-382.
Luz, Z. and S. Meiboom. 1964. "Proton Relaxation in Dilute Solutions of Cobalt(II) and Nickel(II) Ions in Methanol and the Rate of Methanol Exchange of the Solvation Sphere", *J. Chemical Physics*, vol. 40, pp. 2686-2692.
Caravan, P. et al. 1999. "Gadolinium(III) Chelates as MRI Contrast Agents: Structure, Dynamics, and Applications", *Chem. Rev.*, vol. 99, pp. 2293-2352.
Brasch, Robert C. 1991. "Raionale and Applications for Macromolecular Gd-Based Contrast Agents", *Magnetic Resonance in Medicine*, vol. 22, pp. 282-287.
Micskei, K., et al. 1993. "O NMR Study of Water Exchange on $[Gd(DTPA)(H_2O)]^{2-}$ and $[Gd(DOTA)(H_2O)]^-$ Related to NMR Imaging", *Inorg. Chem.*, vol. 32, pp. 3844-3850.
Laurent, S. et al. 2000. "Synthesis and Characterization of Various Benzyl Diethylenetriaminepentaacetic Acids (dtpa) and their Paramagnetic Complexes, Potential Contrast Agents for Magnetic Resonance Imaging" *Helvetica Chimica Acta.*, vol. 83, pp. 394-406.
Lauffer, Randall B. 1987. "Paramagnetic Metal Complexes as Water Proton Relaxation Agents for NMR Imaging: Theory and Design", *Chem. Rev.*, vol. 87, No. 5, pp. 901-927.
Aime, S. et al. 1992. "Synthesis, Characterization, and $1/T_1$ NMRD Profiles of Gadolinium(III) Complexes of Monoamide Derivatives of DOTA-like Ligands. X-ray Structure of the 10-[2-[[2-Hydroxy-1-(hydroxymethyl)ethyl]amino]-1-[(phenylmethoxy)methyl]-2-oxoethyl]-1,4,7,10-tetraazacyclododecane-1,4,7-triacetic Acid-Gadolinium(III) Complex" *Inorg. Chem.*, vol. 31, pp. 2422-2428.
Brinkley, Michael. 1992. "A Brief Survey of Methods for Preparing Protein Conjugates with Dyes, Haptens, amd Cross-Linking Reagents", *Bioconjugate Chem.* vol. 3, pp. 2-13.
Sieving, Paul F. et al. 1990. "Preparation and Characterization of Paramagnetic Polychelates and Their Protein Conjugates", *Bioconjugate Chem.*, vol. 1, pp. 65-71.
Spanoghe, M. et al. 1992. "Proton Relaxation Exhancement by Means of Serum Albumin and Poly-$_L$-Lysine Labeled With DTPA-$Gd^{3+}$: Relaxivities as a Function of Molecular Weight and Conjugation Efficiency", *Magnetic Resonance Imaging*, vol. 10, pp. 913-917.
Paxton, R.J. 1985. "High-Specific-Activity in-labeled Anticarcinoembryonic Antigen Monoclonal Antibody: Improved method for the Synthesis of Diethylenetriaminepentaacetic Acid Conjugates" *Cancer Research*, vol. 45, pp. 5694-5699.
Aime, S. et al. 1999. "Novel Paramagnetic Macromolecular Complexes Derived from the Linkage of a Macrocyclic Gd(III) Complex to Polyamino Acids Through a Squaric Moiety", *Bioconjugate Chem.*, vol. 10, pp. 192-199.

(Continued)

*Primary Examiner* — Michael G Hartley
*Assistant Examiner* — Lance Rider
(74) *Attorney, Agent, or Firm* — Volpe and Koenig, P.C.

(57) ABSTRACT

A cycloalkyl triamine pentacarboxylate compound coordinating to a metal ion to form a high stability metal complex in serum is provided. The metal complex of the present invention can be used as a contrast agent for magnetic resonance imaging (MRI).

3 Claims, 4 Drawing Sheets

(56) References Cited

OTHER PUBLICATIONS

Moats, Rex A. et al. 1997. "A 'Smart' Magnetic Resonance Imaging Agent That Reports on Specific Enzymatic Activity", *Angew. Chem. Int. Ed. Engl.*, vol. 36, pp. 726-728.

Nivorozhkin, Alexander L. et al. 2001. "Enzyme-Activated $Gd^{3+}$ Magnetic Resonance Imaging Contrast Agents with a Prominent Receptor-Induced Magnetization Enhancement", *Angew. Chem. Int. Ed.*, vol. 40, pp. 2903-2906.

Fulvio, U. et al. 1995. "Novel Contrast Agents for Magnetic Resonance Imaging. Synthesis and Characterization of the Ligand BOPTA and Its Ln(III) Complexes (Ln=Gd, La, Lu). X-ray Structure of Disodium (*TPS*-9-145337286-C-S)-(4-Carboxy-5,8,11-tris(carboxymethly)-1-phenyl-2-oxa-5,8,11-triazatridecan-13-oato(5-)]gadolinite(2-) in a Mixture with Its Enantiomer", *Inorg. Chem.*, vol. 34, pp. 633-642.

Silvio, A. et al. 1996. "Gd(III) complexes as contrast agents for magnetic resonance imaging: a proton relaxation enhancement study of the interaction with human serum albumin", J. Biol. Inorg. Chem., vol. 1, pp. 312-319.

Silvio, A. et al. 1999. "Contrast agents for magnetic resonance angiographic applications: H and O NMR relaxomtric investigations on two gadolinium(III) DTPA-like chelates with high binding affinity to human serum albumin", J. Biol. Inorg. Chem., vol. 4, pp. 766-774.

Wang, Y-M. et al. 2005. "Synthesis and Characterization of the Novel Monoamide Derivatives of Gd-TTDA", Inorganic Chemistry, vol. 44, pp. 383-392.

Caravan, P. et al. 2001. "Thermodynamic Stability and Kinetic Inertness of MS-325, a New Blood Pool Agent for Magnetic Resonance Imaging", Inorganic Chemistry, vol. 40, pp. 2170-2176.

Labelle, M. et al. 2001. "Comparison of Metabolite Levels and Water Diffusion Between Cortical and Subcortical Strokes as Monitored by MRI and MRS", *Investigative Radiology*, vol. 36, pp. 153-163.

\* cited by examiner

CYCLOALKYL TRIAMINE PENTACARBOXYLATE AS LIGANDS FOR PARAMAGNETIC METAL COMPLEXES

FIELD OF THE INVENTION

The present invention relates to a novel compound, the cyclically triamine pentacarboxylate, and more particularly to a paramagnetic metal complex prepared from using the compound as the ligand, which can be used as a contrast agent for magnetic resonance imaging (MRI).

BACKGROUND OF THE INVENTION

In recent years, the magnetic resonance imaging (MRI) has been developed rapidly and become one of the most important techniques for diagnosing diseases. In order to increase sensitivity and accuracy, it is very important to develop a safe, stable, and high relaxivity MRI contrast agent. The general metal ions for MRI contrast agents used include $Mn^{2+}$, $Fe^{3+}$, and $Gd^{3+}$, wherein among the metal ions, $Gd^{3+}$ is the most commonly used one due to its greatest magnetic moment (μM) resulting form the seven unpaired electrons thereof. However, such a cation, $Gd^{3+}$, is not suitable for use alone as a MRI contrast agent due to its greatest toxicity in animal bodies. Therefore, it is necessary to use a ligand to chelate $Gd^{3+}$ to form a stable metal complex to inhibit the toxicity thereof.

To design a new contrast agent for MRI, the stability of the metal complex is the main concern. The contrast agent should be effective during the period of time from injecting it to the body to excreting it from the body. Therefore, stability is required for this residence time. Three factors should be considered to determine the stability of a gadolinium complex in vivo, i.e. the thermodynamic stability constant, the conditional stability constant, and the selectivity constant of the gadolinium complex (Cacheris et al, 1990, Magn. Reson. Imag., vol. 8, p 467), wherein the thermodynamic stability constant represents an affinity of the fully deprotonated ligand and the gadolinium (III), and the conditional stability constant represents a stability constant for the gadolinium complex at the physiological pH in vivo. Since there are other metal ions, such as the calcium ion, the zinc ion, the copper ion, and the iron ion, in the organisms, these mentioned ions would compete with the gadolinium (III) for coordinating with the ligand. Accordingly, if the selectivity of the ligand for the gadolinium complex is lower than the others, the gadolinium (III) will release from the gadolinium complex.

The relaxivity of the metal complex is also an important consideration for designing an MRI contrast agent. Generally, the factors affecting the relaxivity are represented by the following equation:

$$r_1 \approx q(\mu_{eff})^2 \tau_c / r^6$$

wherein q represents the hydration number (the number of the water molecules in the inner-sphere); $\mu_{eff}$ represents the effective magnetic distance of the metal ion (as to the gadolinium ion, $\mu_{eff}$ thereof is 0.94 Bohr Magneton); $\tau_c$ represents the correlation time of a paramagnetic material in a fixed magnetic field; and r represents the distance between the metal ion and the protons of the water molecules in the inner-sphere (as to the $Gd^{3+}OH_2$ system, r thereof is 2.50±0.04 Å, e.g. Schauer C. K. A. et al, 1989, J. Chem. Soc., Dalton Trans, p 185). For the gadolinium complexes with similar functional groups, since the values of $\mu_{eff}$ and r could be considered as constants, the main factors for the relaxivity are q and $\tau_c$.

Mainly the correlation time ($\tau_c$) is influenced by the three factors mentioned below: (1) molecular rotational correlation time, $\tau_r$; (2) the electron longitudinal and transverse spin relaxation time, $T_{1, 2e}$; and (3) the inner-sphere water residence lifetime, $\tau_m$ or exchange rate, $\tau_m^{-1} = k_{ex}$ (Tóth, E. et al, 2001, Coord. Chem. Rev, Vol. 216-217, p 363). The relation is shown by the equation:

$$\tau_c^{-1} = \tau_r^{-1} + T_{ie}^{-1} + \tau_m^{-1} \; i=1,2$$

wherein the relaxivity would be a maximum if the value of correlation time $\tau_c$ equals to the reciprocal value of the proton Larmor frequency. So it is inferred that the optimum value of $\tau_c$ is 7.4 ns while the magnetic field strength is 0.5 T (21 MHz $^1$H frequency) and 2.5 ns while the magnetic field strength is 1.5 T (64.5 MHz).

It is suggested that the longitudinal relaxivity mainly depends on the longitudinal relaxation of bound solvent molecule, $T_{1m}$ and $\tau_m$ (Luz et al., 1964, Chem. Phys. Vol. 40, p 2686). The relation is shown by the following equation:

$$r_1 = \frac{1}{T_1} = \frac{qP_m}{T_{1m} + \tau_m}$$

where $P_m$ is the mole fraction of the bound solvent molecules. From the above-mentioned equation, it appears that if the exchange rate of water molecule is very fast, i.e. $\tau_m \ll T_{1m}$, then $r_1$ mainly depends on the relaxivity of the bound solvent molecule ($1/T_{1m}$). Therefore, in order to achieve a higher relaxation rate, a very small value of $\tau_m$ of the gadolinium complex is usually required. However, if $\tau_m$ is too small, then $T_{1m}$ would be influenced by $\tau_m$, so a higher relaxivity is unachievable even though the value of $\tau_m$ is reduced unlimitedly. Through a theoretical simulation for the influence of $T_{1e}$, $\tau_r$, and $\tau_m$ on relaxivity, it is obtained that the optimum value of $\tau_m$ is 10 ns under the condition of simulating q=1 and r=3.1 Å while the magnetic field strengths are respectively 0.5 T and 1.5 T, i.e. the most commonly used two magnetic field strengths in clinical (Caravan et al., 1999, Chem. Rev. Vol. 99, p 2293).

Generally speaking, the augmentation of the magnetic field strength would lead to an increase of $T_{1e}$. $T_{1e}$ has a great influence on the relaxivity in a magnetic field of 0.5 T. However, $T_{1e}$ does not have a very obvious influence on the relaxivity in a magnetic field of 1.5 T. That is, the relaxivity is only influenced by $\tau_r$ and $\tau_m$ while the magnetic field strength is higher. The optimum value of $\tau_m$ is about 10 ns as mentioned in the previous paragraph, whereas the optimum value of $\tau_r$ is about 20 ns. The longitudinal relaxation rates of all available MRI contrast agents in the market now are somewhat lower than their theoretical maximum values. This is mainly because the molecular rotational correlation time values of these contrast agents are small.

The new generation of MRI contrast agents relates to a conjugation of the metal complex of small molecules (with a low molecular weight), such as $[Gd(DOTA)]^{2-}$ or $[Gd(DOTA)]^-$ (Brasch, 1991, Magn. Reson. Med., Vol. 22, p 282), with something with a high molecular weight, so as to adjust their biophysical and pharmacological properties. From the view of biophysics, the molecular rotational correlation time of the contrast agent is lowered by means of the combination of the gadolinium complex of small molecules and the polymeric materials, and the relaxivity is thus increased. Besides, if the gadolinium complexes are combined with tissue-specific targeting moieties, these polymeric conjugations will bring the gadolinium complexes to receptors at low concentration by carriers, so that the receptors would be observed in MRI. Besides, because the molecules of the conjugations with high molecular weights are bigger, they would stay in vascular for a longer time, and thus they are suitable for use in the blood pool imaging.

Misckei K. H. et al. have disclosed the complex [Gd(DTPA)(H$_2$O)]$^{2-}$ with a $\tau_m$ equal to 303 ns, which is much greater than the optimum $\tau_m$ (Micskei K. H. et al., 1993, Inorg. Chem., Vol. 32, p 3844). Laurent S. E. et al. have disclosed the complex [Gd(DTPA)(H$_2$O)]$^{2-}$ with a $\tau_r$ equal to 59 ps, which is much smaller than the optimum $\tau_r$ (Laurent S. E. et al., 2000, Helv. Chim. Acta, Vol. 83, p 394). Hence, the scientists in the field are enthusiastically seeking for a metal complex with the high water exchange rate and the low rotational correlation time, whereby increasing of the relaxivity $r_1$ for the metal complex is desired.

A lot of efforts have been spent on trying to lower the molecular rotational correlation time of the contrast agent in order to increase the relaxivity thereof. For example, the molecular rotational correlation time is lowered by substituting one of the carboxylate in the structure of 1,4,7,10-tetrakis (carboxymethyl)-1,4,7,10-tetraazacyclododecane (DOTA) with larger functional groups containing benzenes. Because of the increase of the value of $\tau_r$, the value of $r_1$ climbs according to the increase of the molecular weights of the ligands (Lauffer et al., 1987, Chem. Rev., Vol. 87, p 901; Aime et al., 1992, Inorg. Chem., Vol. 31, p 2422).

There are many methods developed for linking the gadolinium complex to a high molecular weight residue (Brinkley, 1992, Bioconjugate Chem., Vol. 3, p 2), wherein the acylation, the alkylation, the formation of ureas, and the reduction of amination are popular applied. The most frequently used reagents to be combined with a high molecular weight moiety include DTPA, the derivatives thereof, and DTPA-dianhydride. By the reaction of the primary amine in the high molecular weight moiety with DTPA, the derivatives thereof, or DTPA-dianhydride, the ligands would be combined therewith. Sieving et al. (1990, Bioconjugate Chem., Vol. 1, p 65) disclose the reaction of polylysines with variant molecular weights with DTPA-dianhydride and the derivatives of DTPA. However, the cross-linking always happens very easily during the combination of DTPA-dianhydrare and proteins. Therefore, by the reaction of N-hydroxysuccinimide with DTPA to form a N-hydroxysuccinic ester, the crossing-linking is evitable (Spanoghe et al., 1992, Magn. Reson. Imaging, Vol. 10, p 913). Paxton et al. (1985, Cancer Res., Vol. 45, p 5694) disclose that [DTPA-(N-hydroxysuccinic ester)] would form a covalent binding not only with the protein but also with the monoclonal antibody, and by this carrier the contrast agent would be brought to the anticarcinoembryonic antigen. However, this synthetic method also leads to the production of peptide bonds, so that the binding ability of this ligand to the gadolinium complex is weakened. In order to overcome this problem, Aime et al. (1999, Bioconjugate Chem., Vol. 10, p 192) disclose a method in which the covalent binding is formed between 1,4,7-trikis(carboxymethyl)-1,4,7,10-tetraazacyclododecane (DO3A) and proteins with a linker of 3,4-diethoxycyclobut-3-ene-1,2-dione,squarate. Through this method, the stability of the metal complex is enhanced, and the relaxivity of the gadolinium complex is also increased due to the augment of the molecular weight. In addition, a specific bioactive is achieved via the formation of the covalent binding with the protein.

Because the concentration at which MRI contrast agent is capable of targeting lesions (such as receptors or antigens) falls in a nanomolar level, which is too low for the receptor-induced magnetization enhancement (RIME) to be used in MRI, during the recent years scientists have tried to use the enzyme to activate the gadolinium complex so as to increase the concentration of the contrast agent at the targeted location approximately. Through the method, the relaxation rate of the metal complex is increased, and the target-to-background ratio is also enhanced. Furthermore, 4,7,10-tri(aceticacid)-1-(2-β-galactopyranosylethoxy)-1,4,7,10-tetraazacyclododecane gadolinium (III), Egad, is synthesized by connecting one of the functional groups to the macrocyclic ligand (Moats et al., 1997, Chem. Int. Engl., Vol. 36, p 726). In this case, because Egad is in the form of 9-coordinate, the number of inner space water molecules of Egad is 0.7. That is to say, when Egad enters the organism and meets the β-galactosidase (β-gal), the o-nitrophenyl-β-galactopyranoside in the Egad would be hydrolyzed and removed so as to be bound with 1.2 inner space water molecules, and the MRI signals are thus enchanced.

The Pro-RIME with an increased receptor-induced magnetization is also synthesized (Nivorozhkin et al., 2001, Angew. Chem. Int. Ed., Vol. 15, p 2903). This reagent is composed of: (1) a masking group consisting of three lysine residues, (2) an HSA binding site, (3) a glycine linker, and (4) a signal generation group. The mechanism of action involves that the degradation of lysines in the outermost space is easily achieved by the human carboxypeptidase B thrombin-activatable fibrinolysis inhibitor (TAFI). Once the degradation of the three lysine residues is completed, the exposed lipid soluble aromatics would produce a great binding ability with HSA, and thus a higher relaxation rate is achieved.

A novel MRI contrast agent [Gd(BOPTA)]$^{2-}$, which is capable of forming a stable complex with its relaxivity valued 4.39 mM$^{-1}$ s$^{-1}$ higher than that of [Gd(DTPA)]$^{2-}$ (3.77 mM$^{-1}$ s$^{-1}$), has been disclosed by Fulvio U. et al. In that research, it is found that the inner-sphere water residence lifetime, $\tau_m$, is 289 ns, which is much higher than the theoretical optimum value, 10 ns. In addition, the relaxivity valued 33.0 mM$^{-1}$ s$^{-1}$ for the combination of the mentioned agent [Gd(DTPA)]$^{2-}$ with human serum albumin is also lower than that of MS-325 (47.0 mM$^{-1}$ s$^{-1}$) (Fulvio U. et al., 1995, Inorg. Chem., Vol. 34, p 633).

The process for the preparation of [Gd(BOPTA)]$^{2-}$ has been disclosed in the U.S. Pat. No. 6,162,947 by Marina A. et al. In the mentioned patent, the preparation processes and the advantages of [Gd(BOPTA)]$^{2-}$ are disclosed in detail, and a best process for preparing [Gd(BOPTA)]$^{2-}$ is summarized therein.

The binding constants with HSA, $K_A$ of [cis-Gd(DOTA-BOM$_2$)]$^-$, [trans-Gd(DOTA-BOM$_2$)]$^-$, [Gd(DOTA-BOM$_3$)]$^-$, [Gd(DTPA-BOM$_3$)]$^{2-}$ and MS-325 are 3.2±0.4× 10$^2$M$^{-1}$, 3.6±0.4×10$^2$M$^{-1}$, 1.7±0.1×10$^3$ M$^{-1}$, 4.0±0.3×10$^4$ M$^{-1}$ and 3.0±0.2×10$^4$ M$^{-1}$, respectively; the bound relaxivities, $r_1^b$, of the above-mentioned complexes are 35.7 mM$^{-1}$ s$^{-1}$, 44.2 mM$^{-1}$ s$^{-1}$, 53.2 mM$^{-1}$ s$^{-1}$, 44.0 mM$^{-1}$ s$^{-1}$ and 47.0 mM$^{-1}$ s$^{-1}$, respectively (Silvio A. et al., 1996, J. Biol. Inorg. Chem., Vol. 1, p 312; 1999, J. Biol. Inorg. Chem., Vol. 4, p 766). In the mentioned researches, it is found that the binding constant and the bound relaxivity are increased with the number of the benzyloxymethyl group of the complex.

A novel MRI contrast agent [Gd(AAZTA)]-(1,4-bis(t-butoxycarbonylmethyl)-6-[bis(t-butoxycarbonylmethyl)]) amino-6-methylperhydro-1,4-diazepine, AAZTA) synthesized by Silvio A. et al., has three nitrogen and four carboxylic group included, and is capable of coordinating with gadolinium (III) for forming a complex with seven coordinates. The occurrence of q=2 (in which q is the number of the water molecules) has been assessed by measuring Dy (III) induced $^{17}$O NMR water shift (which is performed by the d.i.s. measurement). The relaxivity of [Gd(AAZTA)]$^-$ is 7.1 mM$^{-1}$ s$^{-1}$ at 20 MHz and 298 K, which is obviously higher than the relaxivity valued 3.89 mM$^{-1}$ s$^{-1}$ of [Gd(DPTA)]$^{2-}$. As to the thermodynamic stability, a log $K_{GdL}$ value of 19.26 for [Gd (DPTA)]²⁻ complex was obtained, where such a value is slightly smaller than [Gd(DTPA)]²⁻ (logK$_{GdL}$=22.46) but is significantly higher than that of [Gd(DTPA-BMA)] (logK$_{GdL}$=16.85). According to the mentioned data, it is concluded by the researcher that [Gd(AAZTA)]⁻ complex with high stability is qualified for serving as an MRI contrast agent. In addition, τ$_r$=74 ps and τ$_m$=90 ns for [Gd(AAZTA)]⁻ system have been obtained by NMRD data. Moreover, a high relaxivity value of 100 mM⁻¹ s⁻¹ has been calculated by simulating the NMRD profile in the situation that τ$_r$ is increased to 30 ns.

Currently, the six MRI contrast agents approved by FDA for clinical usage in intravenous injection include [Gd(DTPA)]²⁻ (gadopentetate dimeglumine), [Gd(DOTA)]⁻ (gadoterate megulumine), [Gd(DTPA-BMA)] (bis-methylamide gadodiamide injection), [Gd(HP-DO3A)] (gadoteridol), [Gd(BOPTA)]²⁻ (gadobenate dimeglumine), and MnDPDP (Teslascan). The above-mentioned agents are extracellular agents, wherein [Gd(DTPA-BMA)] and [Gd(HP-DO3A)] are nonionic contrast agents; [Gd(DTPA)]²⁻, [Gd(DOTA)]⁻ and MnDPDP are ionic contrast agents; [Gd(DOTA)]⁻ and [Gd(HP-DO3A)] have macrocyclic structure; and MnDPDP, [Gd(DTPA)]²⁻ and [Gd(DTPA-BMA)] have the open-chained structures.

A derivative of DTPA, 3,6,10-tri-(carboxymethyl)-3,6,10-triazadodecanedioic acid (TTDA), has been synthesized and the physical and chemical properties of the metal complexes of Gd³⁺, Zn²⁺, Ca²⁺ and Cu²⁺ formed therewith are also studied in detail by Wang et al. The studies show that [Gd(TTDA)]²⁻ has better physical and chemical properties than [Gd(DTPA)]²⁻, so it has a great potential to be an MRI contrast agent (Wang et al., 1998, J. Chem. Soc. Dalton Trans., p 4113-4118).

Based on the above, gadolinium (III) complexes with a high stability and a high relaxivity are the emphases of research during the recent years. It is important and useful to find better MRI contrast agents. Hence the present invention provides new metal complexes with potentiality and high stability as the MRI contrast agents.

SUMMARY OF THE INVENTION

The present invention relates to the cycloalkyl triamine pentacarboxylate compound, and the compound further reacts with a central metal ion for forming a metal complex with high relaxivity. More particularly, the present invention relates to using the paramagnetic metal complexes as the magnetic resonance imaging (MRI) contrast agent.

It is an aspect of the present invention to provide a kind of paramagnetic metal complex with high relaxivity, which is used as a MRI contrast agent.

It is another aspect of the present invention to provide a cycloalkyl triamine pentacarboxylate compound represented by a formula (I):

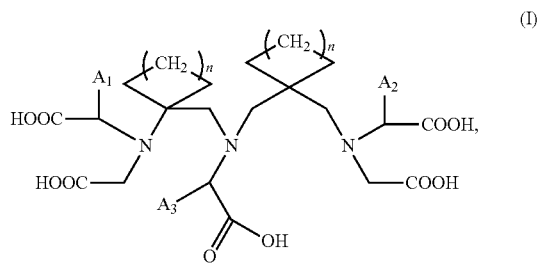

wherein A₁, A₂ and A₃ are substituents for combination with a biocompatible molecule.

Preferably, n is an integer from 1 to 3.

Preferably, A₁, A₂ and A₃ are ones selected from the group consisting of methyl, benzyl, 2-methyoxybenzyl, diphenylmethyl, isothiocyanato-benzyl and 3,5-diiodo-4-hydroxybenzyl.

It is a further aspect of the present invention to provide a metal complex serving as a contrast agent for magnetic resonance imaging (MRI) and represented by a formula ML, wherein M is a central metal ion selected from the group consisting of lanthanide ions, manganese ion, iron ion, cobalt ion, copper ion, nickel ion, and a chromium ion; and L is a ligand with a compound represented by a formula (I):

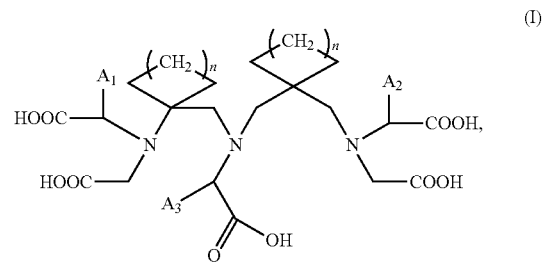

wherein A₁, A₂ and A₃ are substituents for combination with a biocompatible molecular.

Preferably, the central metal ion is one selected from the group consisting of gadolinium (III), iron (III), and manganese (II).

Preferably, n is an integer from 1 to 3.

Preferably, A₁ is one selected from the group consisting of methyl, isothiocyanato-benzyl and 3,5-diiodo-4-hydroxybenzyl.

Preferably, either one of A₂ and A₃ is one of benzyloxymethyl and hydrogen.

In the present invention, it is found that the mentioned cycloalkyl triamine pentacarboxylate compounds provided according to the present invention have the following properties:

1. It has a higher selectivity with the gadolinium complex;
2. The stability of the gadolinium complex formed by the mentioned compound is increased with the increased structural rigidity resulting from the cycloalkyl group included therein;
3. The gadolinium complex of the mentioned compound has a high water exchange rate and a high relaxivity.

The above aspects and advantages of the present invention will become more readily apparent to those ordinarily skilled in the art after reviewing the following detailed description and accompanying drawings, in which:

DETAILED DESCRIPTION OF THE INVENTION

The present invention is described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
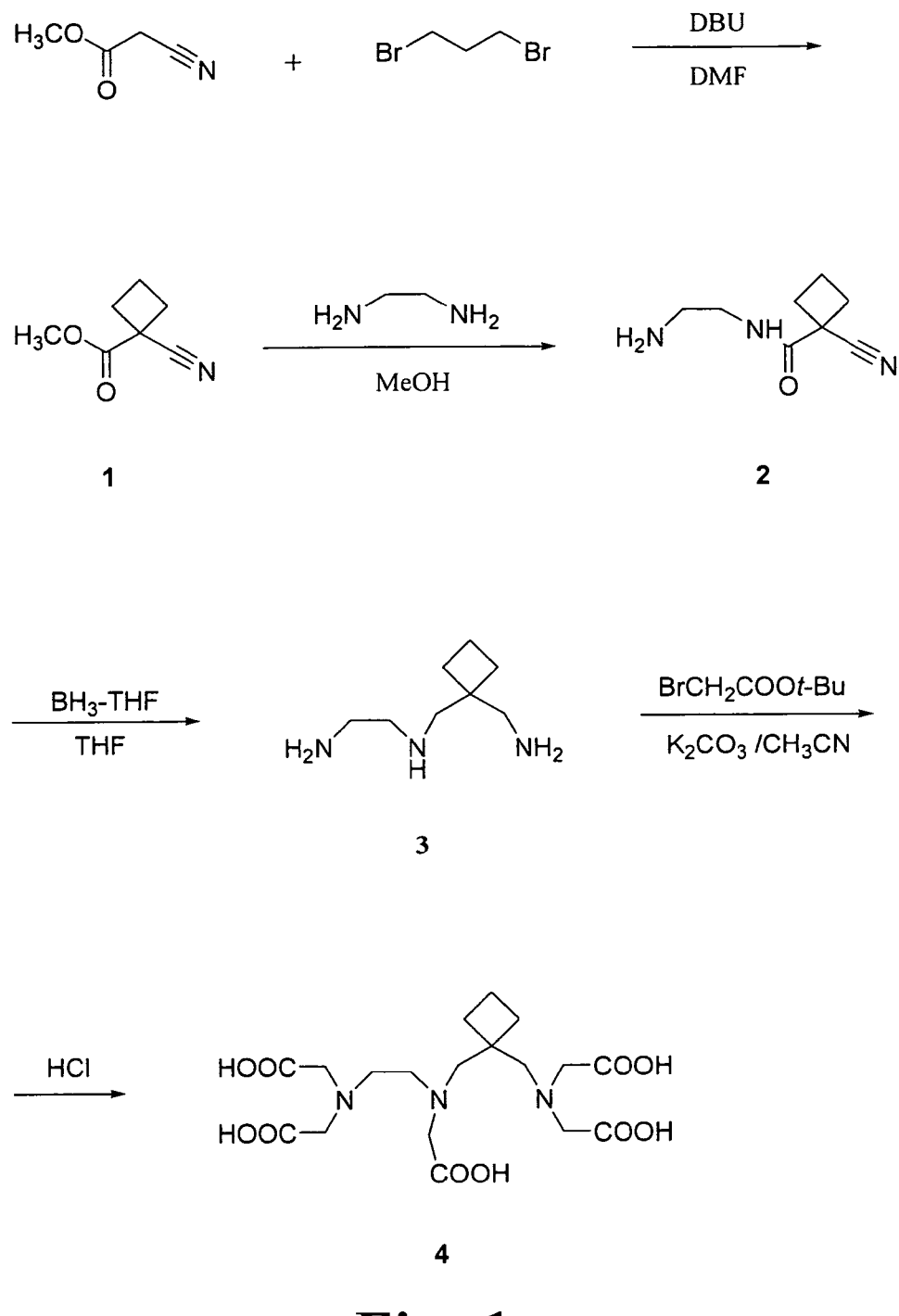
FIG. 1 is a synthetic scheme of cycloalkyl triamine pentacarboxylate compound according to a preferred embodiment of the present invention.

According to the present invention, the synthetic method of cycloalkyl triamine pentacarboxylate compound, CB-TTDA, is described in the following steps shown in FIG. 1. To methyl cyanoacetate (10 g, 0.1 mol) under $N_2$, N,N-dimethylformamide (DMF, 10 mL) was added at room temperature. After 10 min, the solution was added 1,8-diazabicyclo [5,4,0]undec-7-ene (DBU, 33.4 g, 0.22 mol) at 10-20° C., and then reacted 15 min at 50° C. The mixture was cooled to −5 to −10° C., 1,3-dibromopropane (20.4 g, 0.1 mol) in DMF (10 mL) added by syringe, reacted 15 min at room temperature, rose up to 70° C., and then reacted 30 min. The mixture was evaporated and the residue taken up in $H_2O$ and extracted with $CHCl_3$ (3×50 mL). The chloroform phase was evaporated under reduced pressure. The compound 1, i.e. the 1-cyano-cyclobutylcarboxylic acid methyl ester, was purified by column chromatography ($SiO_2$, hexane/acetone 8:1).

A solution of compound 1 (8.74 g, 0.063 mol) in $CH_3OH$ (50 mL) was added to ethylenediamine (3.77 g, 4.25 mL, 0.63 mol) at room temperature. After 15 h at room temperature, the mixture was evaporated. The yellow oil was obtained and dissolved in 20 mL of distilled water, acidulated with HCl to pH 2 and the solution applied to an AG 50W×8 column cation exchange column (200-400 mesh, $H^+$ form, 100 mL of resin, 3.0 cm column diameter). The column was eluted first with $H_2O$ to remove excess ethylenediamine and then with a gradient HCl. The 0.5-1 N HCl solution containing the compound 2, i.e. the 1-cyano-cyclobutylcarboxylic acid(2-amino-ethyl)amide, was evaporated to dryness.

To compound 2 (5.37 g, 0.083 mol) under $N_2$, tetrahydrofuran (THF, 50 ml) was added by syringe. The mixture was cooled to −5 to 0° C., 1M $BH_3$.THF (50 ml) added by syringe, and then the mixture gradually warmed up and brought to reflux for 36 h. Then the solution was evaporated, the residue dissolved in $C_2H_5OH$ (100 mL) and 6N HCl (10 mL), and the resulting solution refluxed for 12 h. The solution was evaporated, the residue dissolved in 20 mL of distilled water, acidulated with HCl to pH 2 and the solution applied to an AG 50W×8 cation exchange resin column (200-400 mesh, $H^+$ form, 100 mL of resin, 3.0 cm column diameter). The column was eluted first with $H_2O$ and then with a gradient HCl. The 3.5-4 N HCl solution containing the compound 3, N'-((1-(aminomethyl)-cyclobutyl)methyl)ethane-1,2-diamine, was evaporated to dryness.

To a solution of compound 3 (4.5 g, 0.029 mol) and $K_2CO_3$ (15 g, 0.1 mol) in $CH_3CN$ (250 mL), tert-butyl bromoacetate (21.19 mL, 0.143 mol) was added. The mixture was heated and refluxed for 24 h. The $K_2CO_3$ was removed by filtration through a Büchner funnel and washed with $CH_3CN$ (40 mL). The filtrate was evaporated and the residue taken up in $H_2O$ and extracted with $CHCl_3$ (3×50 mL). The extract was evaporated, the residue dissolved in 2N HCl (100 mL), and the solution stirred for 12 h at room temperature and then evaporated. The residue was dissolved in distilled water (50 mL) and the solution alkalized with ammonia to pH 11.2 and the solution applied to an AG1×8 anion exchange resin column (200-400 mesh, $HCO_2$– form, 60 mL of resin, 3.0-cm column diameter). The column was eluted first with $H_2O$ and then with a gradient formic acid. The 1.1-1.2 N formic acid solution containing the compound 4, i.e. the 6-carboxymethyl-3-{{[1-(N,N-dicarboxymethyl)-2-aminomethyl]-cyclobut-1-yl}-methyl}-3,6-diazaoctanedioic acid, CB-TTDA was evaporated to dryness and the trace of formic acid was removed by the co-evaporation with 200 mL of water five times.

The $Gd^{3+}$ complex were prepared by dissolving the CB-TTDA (0.05 mmol) in $H_2O$ (3 ml) and adjusting the pH of the solution to 7.5 with 1 N NaOH. To these solutions, 2.5 ml of an aqueous solution of $GdCl_3$ (0.05 mmol) was added dropwise, maintaining the pH at 7.5 with 1 N NaOH. The $Gd^{3+}$ chelate formations were instantaneous at room temperature. The solution were then evaporated under reduced pressure, and the colorless crystals of $[Gd(CB-TTDA)]^{2-}$ is obtained thereby.

In this embodiment, the mentioned process of "extract" means to extract the solution through the deionized water and ethyl acetate, through the deionized water and trichloromethane, or through deionized water, sodium bicarbonate, and saturated salt solution, which depends on the properties of the product to be extracted. Besides, the pH value is adjusted to 8 so that the solid would precipitate first, and then the pH value of the solution is adjusted to 7.

Discussion of the Protonation Constant:

Firstly, the ligands ($H_nL$) are deprotoned ($L^{n-}$) by treating them with the alkaline solution. After that, a slow addition of the acidic solution for associating the deprotonated ligand with the protons ($H^+$) is performed, and thus protonated organic ligands are formed. The equation for the protonation constant is shown as follows:

$$K_i^H = \frac{[H_iL]}{[H_{i-1}L][H]}, \text{ where } i = 1, 2, 3, 4$$

Figure 2:
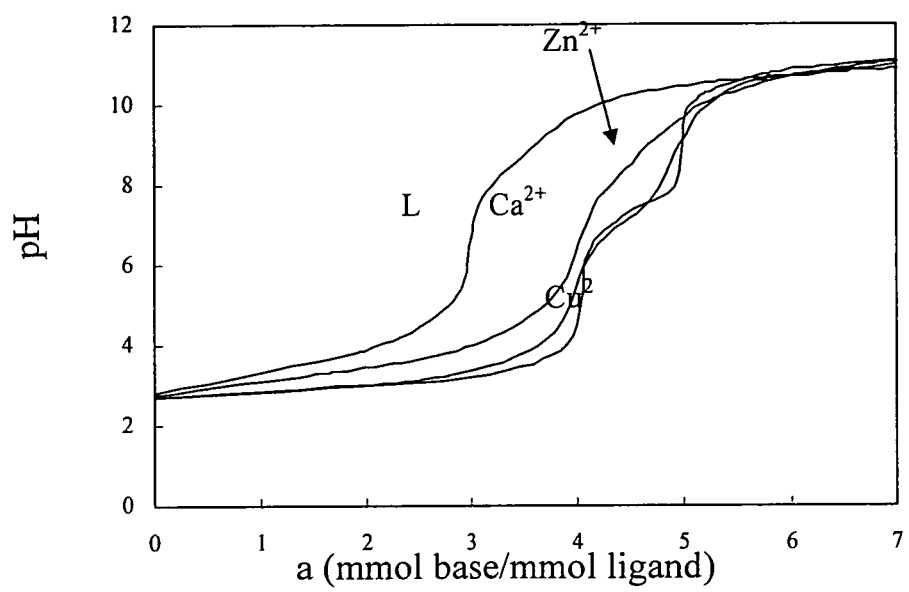
FIG. 2 is a potentiometric titration curve for cycloalkyl triamine pentacarboxylate compound according to a preferred embodiment of the present invention measured by an automatic titrator system.

Please refer to FIG. 2, which is a potentiometric titration curve for CB-TTDA (the ionic strength I=0.1 M $Me_4NCl$ and the temperature T=25.0±0.1° C.) measured by an automatic titrator system. The protonation constants for the CB-TTDA are determined from the titration data with the FORTRAN computer program PKAS as shown in Table 1.

TABLE 1

Protonation constants of CB-TTDA, TTDA and DTPA.

| | log $K_n^H$ | | |
|---|---|---|---|
| Equilibrium | CB-TTDA | TTDA | DTPA |
| [HL]/[L][H] | 11.08(0.03) | 10.60 | 10.49 |
| [$H_2$L]/[HL][H] | 9.17(0.05) | 8.92 | 8.60 |
| [$H_3$L]/[$H_2$L][H] | 5.23(0.02) | 5.12 | 4.28 |
| [$H_4$L]/[$H_3$L][H] | 3.11(0.04) | 2.80 | 2.64 |
| ΣpKa | 28.59 | 27.44 | 26.01 |

In the potentiometric titration curve, it is found that the sharper increase of the curves is, the larger difference between the protonation constants thereof will be.

Please refer to FIG. 2, around a=3 (mmol base/mmol ligand), the CB-TTDA curve shows a sharp increase. This is due to the large difference between the second and the third protonation constant values of CB-TTDA (log $K_2^H$=9.17, and log $K_3^H$=5.23).

As to the first protonation constant, the first protonation constant of CB-TTDA is higher than those of the other two ligands, TTDA and DTPA, which are reported by Y. M. Wang et al., Inorganic Chemistry, vol. 44, page 382, 2005 and by P. Caravan et al., Inorganic Chemistry, vol. 44, page 2170, 2001, respectively. This is due to the cyclobutyl group on the carbon chain of the CB-TTDA. The third protonation constant of CB-TTDA is similar to that of TTDA. As to the values of the $\Sigma^{pKa}$, it is shown that CB-TTDA>TTDA>DTPA.

Discussion of the Thermodynamic Stability Constant:

Presently, there are two ways for calculating the thermodynamic stability constant of a metal complex by the potentiometric titration. (1) The direct titration: the metal ion and the ligand in equal molars are mixed previously, the mixture is titrated by KOH in an amount of 0.005 ml per time, and then the titration data are calculated by BEST program for obtaining the thermodynamic stability constant of the metal complexes. (2) The ligand-ligand competition titration: the metal ion, the ligand and the EDTA in equal molars are mixed previously, beyond the titration pH, 10-15 minutes equilibrium period is needed for each time of adding of the basic titrant, and the titration data are calculated by BEST program for obtaining the thermodynamic stability constant of the metal complexes. The second method is suitable for the metal complex whose disassociation rate is less than 25% at low pH (such as pH 2). Take the metal complex of the present invention for instance, since it is not able to form a complex with the ligand at a pH value around 2, the thermodynamic stability constant thereof must be calculated by the previous method. The equation for the thermodynamic stability constant is defined as follows:

$$K_{ML(therm)} = \frac{[ML]}{[M][L]},$$

where M represents the metal ion, L represents the ligand, and ML represents the metal complex.

The potentiometric titration curves for the complexes of $Gd^{3+}$, $Ca^{2+}$ and $Zn^{2+}$ with CB-TTDA (the ionic strength I=0.1M $Me_4NCl$ and the temperature T=25.0±0.1) are shown in FIG. 2. The thermodynamic stability constants for the metal complexes with CB-TTDA are determined from the titration data with the FORTRAN computer program BEST as shown in Table 2 with the reported thermodynamic stability constants of TTDA and DTPA, which are respectively reported by Y. M. Wang et al., Inorganic Chemistry, vol. 44, page 382, 2005 and by P. Caravan et al., Inorganic Chemistry, vol. 44, page 2170, 2001.

TABLE 2

The thermodynamic stability constants, the conditional stability constants, the selectivity constant and the modified selectivity constant for the metal complexes of CB-TTDA, TTDA and DTPA at I = 0.1 M $Me_4NCl$ and T = 25.0 ± 0.1° C.

| Parameter | log $K_{ML}$ | | |
|---|---|---|---|
| | CB-TTDA | TTDA | DTPA |
| [GdL]/[Gd][L] | 20.28(0.03) | 18.96 | 22.46 |
| [CaL]/[Ca][L] | 9.52(0.02) | 9.13 | 10.75 |
| log $K_{CaHL}$ | 6.24(0.02) | 8.20 | 6.11 |
| log $K_{CaL}$ (pH = 7.4) | 4.06 | 4.42 | 6.43 |

TABLE 2-continued

The thermodynamic stability constants, the conditional stability constants, the selectivity constant and the modified selectivity constant for the metal complexes of CB-TTDA, TTDA and DTPA at I = 0.1 M $Me_4NCl$ and T = 25.0 ± 0.1° C.

| Parameter | log $K_{ML}$ | | |
|---|---|---|---|
| | CB-TTDA | TTDA | DTPA |
| [ZnL]/[Zn][L] | 16.06(0.03) | 16.03 | 18.70 |
| log $K_{ZnHL}$ | 8.13(0.04) | 7.80 | 5.60 |
| log $K_{ZnL}$ (pH = 7.4) | 10.60 | 11.32 | 14.38 |
| [CuL]/[Cu][L] | 17.71(0.02) | 16.77 | 21.38 |
| log $K_{CuHL}$ | 5.29(0.03) | 5.69 | 4.81 |
| log $K_{CuL}$ (pH = 7.4) | 12.25 | 12.06 | 17.00 |
| log K(Gd/Ca) | 11.76 | 9.83 | 11.71 |
| log K(Gd/Zn) | 4.22 | 2.93 | 3.76 |
| log K(Gd/Cu) | 2.57 | 2.19 | 1.08 |
| log $K_{sel'}$ | 8.24 | 7.18 | 7.06 |
| pGd | 15.82 | 15.25 | 19.14 |
| pCa | 4.09 | 6.28 | 7.46 |
| pZn | 12.41 | 12.86 | 15.39 |
| pCu | 13.26 | 13.06 | 18.06 |

The thermodynamic stability constant of $[Gd(CB-TTDA)]^{2-}$ is lower than that of $[Gd(DTPA)]^{2-}$ but higher than that of $[Gd(TTDA)]^{2-}$. Based on the result, it seems that the cyclobutyl group on the carbon chain of the metal complex could make the structure thereof become more rigid, thereby increasing the stability constant thereof. In addition, it is found that the value of the thermodynamic stability constants for the metal complexes of $Gd^{3+}$, $Ca^{2+}$, $Zn^{2+}$ and $Cu^{2+}$ with CB-TTDA have the following relationships: $[Gd(CB-TTDA)]^{2-}$ (20.28)>$[Cu(CB-TTDA)]^{3-}$ (17.71)>$[Zn(CB-TTDA)]^{3-}$ (16.06)>$[Ca(CB-TTDA)]^{3-}$ (9.52). This is due to the differences of the charge densities (Z/r) of the metal ions. Generally, the higher the charge densities the metal ion has the more stable it will be. Since the ionic radius for $Gd^{3+}$, $Zn^{2+}$, $Ca^{2+}$ and $Cu^{2+}$ are 1.247, 1.04, 1.26 and 0.87 angstroms, respectively, the sequence of the charge densities for the metal ion from high to low is $Gd^{3+}$, $Cu^{2+}$, $Zn^{2+}$ and $Ca^{2+}$, which is in consistence to the sequence of the thermodynamic stability constants for the metal complexes as shown in Table 2.

Discussion of the Conditional Stability Constant:

The conditional stability of a metal chelate under physiology conditions (pH 7.4) is more important than the thermodynamic stability constant.

The reaction equation for forming the metal complexes by the metals and the ligands are defined as follows:

$$M + L \rightleftharpoons ML,$$

where M represents the metal ion, L represents the ligand, and ML represents the metal complex.

The conditional stability constant ($K_{cond}$) specifies the degree of metal chelation at a given pH and is defined as follows:

$$K_{cond} = \frac{[ML]}{[M]} \{[L] + [HL] + [H_2L] + ...\}^{-1}$$

where the conditional stability constant could be calculated from the thermodynamic stability constant by the equation defined as follows:

$$K_{cond} = K_{therm} \frac{[L]}{[L_T]},$$

where $L_T$ is the total concentration of the uncomplexed ligand, which is defined by the following equation:

$$L_T = \{[L]+[HL]+[H_2L]+\ldots\}$$

and thus $K_{cond} = K_{therm}\{1+K_1^H[H^+]+K_1^H K_2^H [H^+]^2+\ldots\}^{-1} = K_{therm}\alpha_H$, where $\alpha_H = \{1+K_1^H[H^+]+K_1^H H_2^H [H^+]^2+\ldots\}^{-1}$, and the values of the calculated conditional stability constants are $[Gd(DTPA)]^{2-}$ (18.14)>$[Gd(CB-TTDA)]^{2-}$ (15.83)>$[Gd(TTDA)]^{2-}$ (14.25), which means that the compound CB-TTDA of the present invention still forms a very stable metal complex with the gadolinium (III) ion at pH=7.4.

Discussion of the Selectivity Constant:

The toxicity of the MRI contrast agent is mainly coming from the free gadolinium (III) ion released by the MRI contrast agent dissociation. Since the metal ions in vivo, such as the $Zn^{2+}$, $Ca^{2+}$, $Cu^{2+}$, etc., will exchange with the gadolinium (III) ion of the gadolinium (III) complexes, resulting in the releasing of the free gadolinium (III) ion, the free gadolinium (III) ion will form the metal complexes with the amino acids, the citric acids or the albumins in vivo. Accordingly, the toxicity is generated from the physiological imbalance.

Among $Zn^{2+}$, $Ca^{2+}$, $Cu^{2+}$ and other metal ions, the zinc ion is the main cause for causing the gadolinium complex dissociation in vivo, and this is due to the high concentration in plasma thereof that is among 10~50 μM. That is to say, if the zinc ions form the stable metal complexes with the ligands, more free gadolinium ions will be released thereby. Although the copper ions could also form the stable metal complexes with the ligands, the concentration in plasma of the copper ion is only among 1~10 μM, which means the free gadolinium ions replaced thereby are much more less. Although the calcium ion concentration is 2.5~4 mM high in plasma, the stability of the calcium (II) complex is much lower, and thus the calcium ions could not replace the gadolinium ions of the gadolinium complexes.

The selectivity constant is used only for showing the difference between the gadolinium complex and other metal complexes. However, due to the coexistence of the zinc ion, the calcium ion and the copper ion in vivo, all the following factors, which are the pH value, the protonation constant for the ligand, the concentrations of the metal ions ($Zn^{2+}$, $Ca^{2+}$, $Cu^{2+}$) and the stability constants for $Gd^{3+}$, $Zn^{2+}$, $Ca^{2+}$ and $Cu^{2+}$ complexes should be considered for obtaining the selectivity constant with a new definition, called modified selectivity constant ($K_{sel'}$) and defined by the following equation:

$$K_{sel'} = K_{therm}(\alpha_H^{-1} + \alpha_{CaL}^{-1} + \alpha_{CuL}^{-1} + \alpha_{ZnL}^{-1})^{-1},$$

where $$\alpha_H^{-1} = 1 + K_1^H[H^+] + K_1^H K_2^H [H^+]^2 + \ldots;$$

$$\alpha_{CaL}^{-1} = 1 + K_{CaL}[Ca^{2+}];$$

$$\alpha_{CuL}^{-1} = 1 + K_{CuL}[Cu^{2+}];$$

$$\alpha_{ZnL}^{-1} = 1 + K_{ZnL}[Zn^{2+}];$$

and thus the modified selectivity constant of the gadolinium complex at the biological pH (7.4) could be calculated by the mentioned equation (the value of the conditional stability constant is calculated previously, and the concentrations of the zinc, the calcium and the copper ions are 50 μM, 2.5 nM and 1 μm, respectively).

The selectivity constant and the modified selectivity constant for the metal complexes with CB-TTDA, TTDA or DTPA are shown in Table 2. As shown in Table 2, the selectivity constant for zinc (II) of the $[Gd(CB-TTDA)]^{2-}$ is significantly higher than those of $[Gd(TTDA)]^{2-}$ and $[Gd(DTPA)]^{2-}$.

Figure 3:
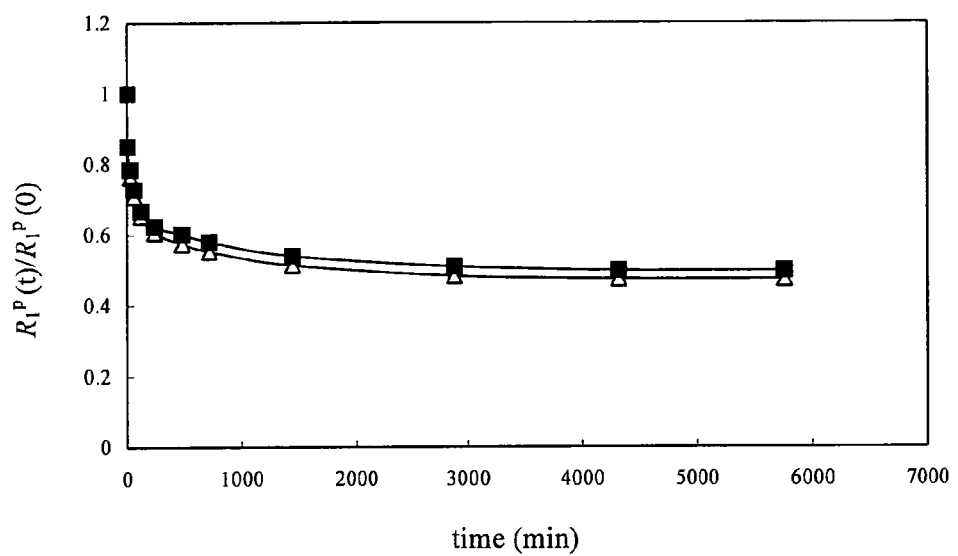
FIG. 3 is a diagram showing the relative water proton paramagnetic longitudinal relaxation rates vs. time for the cycloalkyl triamine pentacarboxylate compound with the zinc (II) according to a preferred embodiment of the present invention.

Discussion of the Kinetic Stability of the Gadolinium Complex:

Among $Zn^{2+}$, $Ca^{2+}$, $Cu^{2+}$ and other metal ions, the zinc (II) combines a rather high concentration with high affinity toward poly(amino carboxylate) and may result in the gadolinium complex dissociation in vivo. In FIG. 3, the longitudinal relaxation time, $T_1(t)$, at different time point of a buffered solution, the phosphate buffer solution at pH 7.4, containing 2.5 mM $ZnCl_2$ and 2.5 mM $[Gd(CB-TTDA)]^{2-}$ is determined at 37.0±0.1° C. and 20 MHz relaxometer. The reciprocal of the longitudinal relaxation time is the water proton paramagnetic longitudinal relaxation rate, $R_1^P(t)$, where the ration of $R_1^P(t)/R_1^P(0)$ represents the stability of the gadolinium complex for $Zn^{2+}$. If $Zn^{2+}$ exchanges with $Gd^{3+}$ in Gd(III) complex, gadolinium phosphate salt will precipitate, which results in the decreasing of the $R_1$. Based on the mentioned principle, the kinetic stability of the gadolinium complex for zinc (II) could be measured.

TABLE 3

The percentage of the ratio of the relaxation rates, $R_1^P{}_{(t=3d)}/R_1^P{}_{(t=0)}$, of the gadolinium complex before and following incubation with zinc (II) solution for three days (20 MHz and 37.0 ± 0.1° C.).

| complex | $R_1^P$ (t = 3days)/$R_1^P$ (t = 0 days) [%] |
|---|---|
| $[Gd(CB-TTDA)]^{2-}$ | 47.4 |
| $[Gd(DTPA)]^{2-}$ | 49.79 |
| [Gd(DTPA-BMA)] | 9 |

In Table 3, the ratio, $R_1^P{}_{(t=3d)}/R_1^P{}_{(t=0)}$, of the relaxation rates in percentage of three gadolinium complexes, $[Gd(CB-TTDA)]^{2-}$, $[Gd(DTPA)]^{2-}$ and [Gd(DTPA-BMA)], before and following incubation with zinc (II) solution for three days (20 MHz and 37.0±0.1° C.) are shown, where the ratios of the relaxation rates in percentage of $[Gd(DTPA)]^{2-}$ and [Gd(DTPA-BMA)] were reported by S. Laurent et al, Invest. Radiol., vol. 36, page 155, 2001.

As shown in Table 3, the ratio of the relation rates in percentage of $[Gd(CB-TTDA)]^{2-}$ (47.4%) is similar to that of the commercial MRI contrast agent, $[Gd(DTPA)]^{2-}$. That is to say, the kinetic stability for $[Gd(CB-TTDA)]^{2-}$ of the present invention is similar to that of $[Gd(DTPA)]^{2-}$. In addition, by comparing the ratio of the relation rates in percentage of $[Gd(CB-TTDA)]^{2-}$ of the present invention with that of another commercial MRI contrast agent, [Gd(DTPA-BMA)], it is clear that the mentioned value of $[Gd(CB-TTDA)]^{2-}$ of the present invention is much higher than that of [Gd(DTPA-BMA)]. Hence, the $[Gd(CB-TTDA)]^{2-}$ of the present invention has good kinetic stability toward zinc (II) transmetallation.

Discussion of the Number of Inner Space Water Molecule:

From measuring the d.i.s. (Dy (III)-induced $^{17}O$-NMR water shifts) of the $^{17}O$ nuclides in water induced by Dy (III) via $^{17}O$-NMR and graphing the concentration of Dy (III) complexes with respect to the d.i.s., a linear relationship is found, as shown in the following equation:

$$d.i.s. = q\Delta[Dy(ligand)_n(H_2O)_q]/[H_2O]$$

Figure 4:
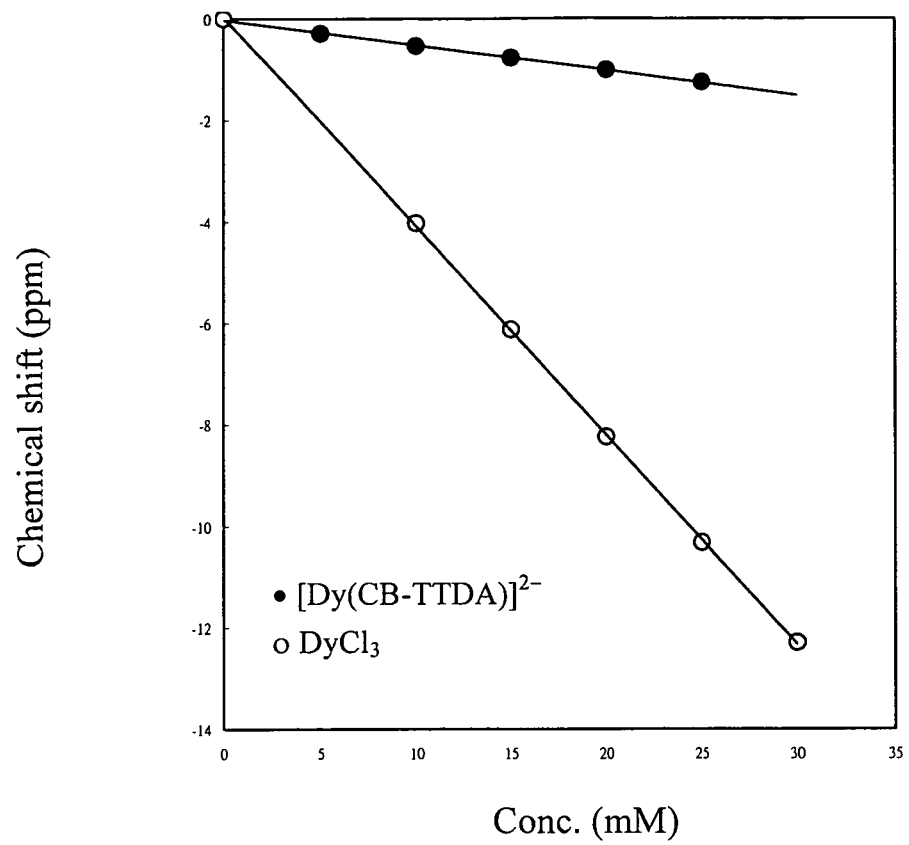
FIG. 4 is a diagram showing the $^{17}$O-NMR chemical shift of the cycloalkyl triamine pentacarboxylate compound according to a preferred embodiment of the present invention.

The slope is $qΔ/[H_2O]$ with q being the number of inner space water molecule. As shown in FIG. 4, the slope of $[Dy(CB-TTDA)]^{2-}$ is −48.2 ppm/mM, while the slope of the Dy (III) induced $^{17}O$ is −414.8 ppm/mM. Because the Dy (III) hydrate is able to combine with 8 water molecules and is in direct proportion to the slope, the value of q (q=0.9) for $[Dy(CB-TTDA)]^{2-}$ is obtained thereby.

The Research of Relaxivity:

Mainly, the relaxivity of paramagnetic metal complex is affected by two factors, the inner-sphere and the outer-sphere relaxivities. Due to the existence of inner water molecules of the ligand of the present invention, the relaxivity thereof is mainly affected by the change of the inner-sphere relaxivity rather than the outer-sphere relaxivity (the outer-sphere relaxivity is considered similar to other ligands). The longitudinal relaxation time of $[Gd(CB-TTDA)]^{2-}$ measured by 20 MHz relaxometer at 37.0±0.1° C. is shown in Table 4. The relaxivity of $[Gd(CB-TTDA)]^{2-}$ is higher than those of $[Gd(TTDA)]^{2-}$ (Y. M. Wang et al., Inorganic Chemistry, vol. 44, page 382, 2005) and $[Gd(DTPA)]^{2-}$ (P. Caravan et al., Inorganic Chemistry, vol. 44, page 2170, 2001).

TABLE 4

The relaxivities ($r_1$) of $[Gd(CB-TTDA)(H_2O)]^{2-}$, $[Gd(TTDA)(H_2O)]^{2-}$ and $[Gd(DTPA)(H_2O)]^{2-}$ at 20 MHz and 37.0 ± 0.1° C.

| Complex | pH | relaxivity $r_1/mM^{-1}s^{-1}$ |
|---|---|---|
| $[Gd(CB-TTDA)(H_2O)]^{2-}$ | 7.4 ± 0.1 | 4.12 ± 0.05 |
| $[Gd(TTDA)(H_2O)]^{2-}$ | 7.5 ± 0.1 | 3.85 ± 0.03 |
| $[Gd(DTPA)]^{2-b}$ | 7.6 ± 0.1 | 3.89 ± 0.03 |

There are several preferred embodiments below. They are just the illustrations of the methods, the characteristics, and the advantages according to the present invention.

The synthesis of ligand—cycloalkyl triamine pentacarboxylate:

EXAMPLE 1

The Synthetic Method of 1-cyano-cyclobutyl-carboxylic acid methyl ester, the Compound 1

To methyl cyanoacetate (10 g, 0.1 mol) under $N_2$, N,N-dimethylformamide (DMF, 10 mL) was added at room temperature. After 10 min, the solution was added 1,8-diazabicyclo [5,4,0]undec-7-ene (DBU, 33.4 g, 0.22 mol) at 10-20° C., and then reacted 15 min at 50° C. The mixture was cooled to −5 to −10° C., 1,3-dibromopropane (20.4 g, 0.1 mol) in DMF (10 mL) added by syringe, reacted 15 min at room temperature, rose up to 70° C., and then reacted 30 min. The mixture was evaporated and the residue taken up in $H_2O$ and extracted with $CHCl_3$ (3×50 mL). The chloroform phase was evaporated under reduced pressure. The compound 1 was purified by column chromatography ($SiO_2$, hexane/acetone 8:1), yielding 8.74 g (62.81%). MS (ESI): m/z: 140.08 $[M+H]^+$. Anal. Calcd (Found) for $C_7H_9NO_2$: C, 60.42 (60.74); H, 6.52 (6.58); N, 10.07 (10.21). $^1H$ NMR ($D_2O$, 400 MHz), δ ((ppm): 3.84 (s, 3H, —$OCH_3$), 2.73-2.63 (m, 4H, —C—$CH_2$—$CH_2$—), 2.17-2.32 (m, 2H, —C—$CH_2$—$CH_2$—$CH_2$—). $^{13}C$ NMR ($D_2O$, 400 MHz), δ (ppm): 169.17, 128.11, 53.50, 39.38, 31.22, 17.18.

EXAMPLE 2

The Synthetic Method of 1-cyano-cyclobutyl carboxylic acid (2-amino-ethyl) amide, the Compound 2

A solution of compound 1 (8.74 g, 0.063 mol) in $CH_3OH$ (50 mL) was added to ethylenediamine (3.77 g, 4.25 mL, 0.63 mol) at room temperature. After 15 h at room temperature, the mixture was evaporated. The yellow oil was obtained and dissolved in 20 mL of distilled water, acidulated with HCl to pH 2 and the solution applied to an AG 50W×8 column cation exchange column (200-400 mesh, $H^+$ form, 100 mL of resin, 3.0 cm column diameter). The column was eluted first with $H_2O$ to remove excess ethylenediamine and then with a gradient HCl. The 0.5-1 N HCl solution containing the product was evaporated to dryness, yielding 6.37 g (60.47%). MS (ESI): m/z: 168.08 $[M+H]^+$. Anal. Calcd (Found) for $C_8H_{13}N_3O$: C, 57.46 (57.02); H, 7.84 (7.49); N, 25.13 (24.88). $^1H$ NMR ($D_2O$, 400 MHz), δ (ppm): 3.46 (t, J=6.0 Hz, 2H, —$NHCH_2CH_2NH_2$), 3.07 (t, J=6.0 Hz, 2H, —$NHCH_2CH_2NH_2$), 2.60-2.50 (m, 4H, —$CCH_2CH_2CH_2$—), 1.94-2.14 (m, 2H, —$CCH_2CH_2CH_2$—). $^{13}C$ NMR ($D_2O$, 400 MHz), δ (ppm): 168.99, 119.95, 41.39, 40.59, 39.38, 31.13, 17.09.

EXAMPLE 3

The Synthetic Method of N'-((1-(amino methyl)-cyclobutyl)methyl) ethane-1,2-diamine, the Compound 3

To compound 2 (5.37 g, 0.083 mol) under $N_2$, tetrahydrofuran (THF, 50 ml) was added by syringe. The mixture was cooled to −5 to 0° C., 1M $BH_3$.THF (50 ml) added by syringe, and then the mixture gradually warmed up and brought to reflux for 36 h. Then the solution was evaporated, the residue dissolved in $C_2H_5OH$ (100 mL) and 6N HCl (10 mL), and the resulting solution refluxed for 12 h. The solution was evaporated, the residue dissolved in 20 mL of distilled water, acidulated with HCl to pH 2 and the solution applied to an AG 50W×8 cation exchange resin column (200-400 mesh, $H^+$ form, 100 mL of resin, 3.0 cm column diameter). The column was eluted first with $H_2O$ and then with a gradient HCl. The 3.5-4 N HCl solution containing the product was evaporated to dryness, yielding 2.98 g (50.0%). MS (ESI): m/z: 158.23 $[M+H]^+$. Anal. Calcd (Found) for $C_9H_{19}N_3$: C, 61.10 (60.83); H, 12.18 (12.41); N, 26.72 (26.36). $^1H$ NMR ($D_2O$, 400 MHz), δ (ppm): 3.39-3.33 (m, 4H, —$NHCH_2CH_2NH_2$), 3.25 (s, 2H, —$NH_2CH_2CCH_2NH$—), 3.16 (s, 2H, —$NH_2CH_2CCH_2NH$—), 1.95-1.86 (m, 6H, —$CCH_2CH_2CH_2$—). $^{13}C$ NMR ($D_2O$, 400 MHz), δ (ppm): 52.73, 45.51, 43.64, 38.32, 35.50, 26.64, 14.16.

EXAMPLE 4

The synthetic method of 6-carboxymethyl-3-{{[1-(N,N-dicarboxymethyl)-2-aminomethyl]-cyclobut-1-yl}-methyl}-3,6-diazaoctanedioic acid CB-TTDA, the compound 4

To a solution of compound 3 (4.5 g, 0.029 mol) and $K_2CO_3$ (15 g, 0.1 mol) in $CH_3CN$ (250 mL), tert-butyl bromoacetate (21.19 mL, 0.143 mol) was added. The mixture was heated and refluxed for 24 h. The $K_2CO_3$ was removed by filtration through a Büchner funnel and washed with $CH_3CN$ (40 mL). The filtrate was evaporated and the residue taken up in $H_2O$ and extracted with CHCl$_3$ (3×50 mL). The extract was evaporated, the residue dissolved in 2N HCl (100 mL), and the solution stirred for 12 h at room temperature and then evaporated. The residue was dissolved in distilled water (50 mL) and the solution alkalized with ammonia to pH 11.2 and the solution applied to an AG1×8 anion exchange resin column (200-400 mesh, HCO$_2$– form, 60 mL of resin, 3.0-cm column diameter). The column was eluted first with H$_2$O and then with a gradient formic acid. The 1.1-1.2 N formic acid solution containing the product was evaporated to dryness and the trace of formic acid was removed by the co-evaporation with 200 mL of water five times, yielding 4.15 g (31.98%). MS (ESI): m/z: 448.34 [M+H]$^+$. Anal. Calcd (Found) for C$_{18}$H$_{29}$N$_3$O$_{10}$: C, 48.32 (48.03); H, 6.53 (6.82); N, 9.39 (9.63). $^1$H NMR (D$_2$O, 400 MHz), δ (ppm): 3.90 (s, 4H, —CH$_2$COOH), 3.79 (s, 4H, —CH$_2$COOH), 3.65 (s, 2H, —NH$_2$CH$_2$CCH$_2$NH—), 3.55 (s, 2H, —NH$_2$CH$_2$CCH$_2$NH—), 3.41 (s, 4H, —NHCH$_2$CH$_2$NH$_2$), 3.37 (s, 2H, —CH$_2$COOH), 1.99 (m, 6H, —CCH$_2$CH$_2$CH$_2$—). $^{13}$C NMR (D$_2$O, 400 MHz), δ (ppm): 171.61, 171.48, 170.15, 61.36, 61.08, 56.62, 56.23, 53.73, 51.17, 50.16, 38.41, 30.86, 15.92.

EXAMPLE 5

Preparation of Gadolinium Complex, the Cycloalkyl Triamine Pentacarboxylate Complex, [Gd(CB-TTDA)]$^{2-}$ The Gd$^{3+}$ complex were prepared by dissolving the CB-TTDA (0.05 mmol) in H$_2$O (3 ml) and adjusting the pH of the solution to 7.5 with 1 N NaOH. To these solutions, 2.5 ml of an aqueous solution of GdCl$_3$ (0.05 mmol) was added dropwise, maintaining the pH at 7.5 with 1 N NaOH. The Gd$^{3+}$ chelate formations were instantaneous at room temperature. The solution were then evaporated under reduced pressure, and 0.081 g of transparent crystals is precipitated with a yield value of 90.3%.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cycloalkyl triamine pentacarboxylate compound represented by a formula (I):

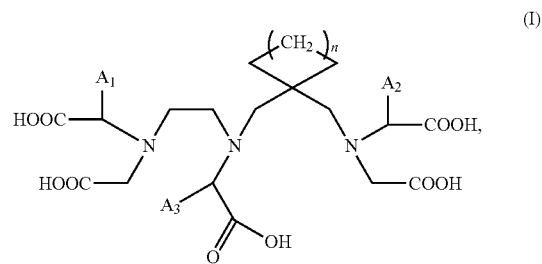

wherein A$_1$, A$_2$ and A$_3$ are selected from a group consisting of methyl, benzyl, 2-methyoxybenzyl, diphenylmethyl, isothiocyanato-benzyl, 3,5-diiodo-4-hydroxybenzl, benzyloxmethyl and hydrogen, and n is 1.

2. A metal complex serving as a contrast agent for magnetic resonance imaging (MRI) and represented by a formula ML, wherein M is a central metal ion selected from the group consisting of lanthanide series ions, manganese ion, iron ion, cobalt ion, copper ion, nickel ion, and chromium ion; and L is a ligand with a compound represented by a formula (I):

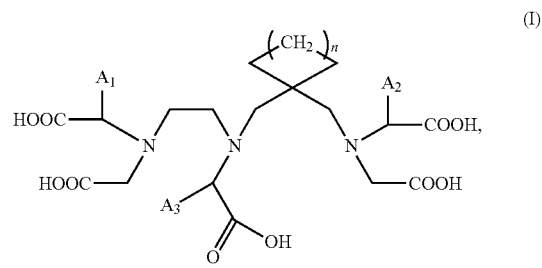

wherein A$_1$, A$_2$ and A$_3$ are selected from a group consisting of methyl, benzyl, 2-methyoxybenzyl, diphenlymethyl, isothiocyanato-benzl, 3,5-diiodo-4-hydroxybenzl, benzyloxmethyl and hydrogen, and n is 1.

3. The metal complex according to claim 2, wherein the central metal ion is one selected from the group consisting of gadolinium ion, iron ion, and manganese ion.

* * * * *